US00PP29804P2

(12) United States Plant Patent
Smith

(10) Patent No.: US PP29,804 P2
(45) Date of Patent: Nov. 6, 2018

(54) ***CHRYSANTHEMUM* PLANT NAMED 'CIFZ0058'**

(50) Latin Name: *Chrysanthemum x morifolium*
Varietal Denomination: CIFZ0058

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,554

(22) Filed: Jan. 27, 2017

(51) Int. Cl.
*A01H 5/02* (2018.01)

(52) U.S. Cl.
USPC ..... Plt./287

(58) Field of Classification Search
USPC ..... Plt./287, 292, 291
CPC ..... A01H 5/0255; A01H 5/02; A01H 5/025; A01H 5/00; A01H 6/1424
See application file for complete search history.

*Primary Examiner* — June Hwu
(74) *Attorney, Agent, or Firm* — Dale Skalla

(57) ABSTRACT

A new garden type *Chrysanthemum* plant named 'CIFZ0058' particularly distinguished by the medium (1.75 inch) sized purple decorative flowers, a compact sized plant with round mound habit and a natural season response in early September.

1 Drawing Sheet

Figure 1:
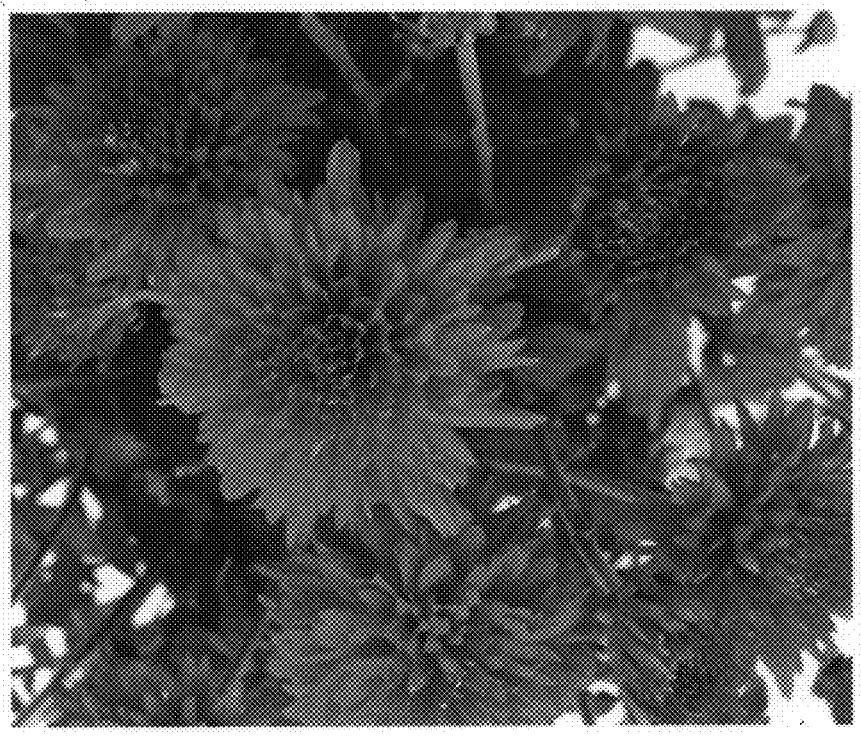

Latin name of the genus and species of the plant claimed: *Chrysanthemum* x *morifolium.*

Varietal denomination: 'CIFZ0058'.

BACKGROUND OF THE NEW PLANT

The present invention comprises a new *Chrysanthemum*, botanically known as *Chrysanthemum* x *morifolium*, and hereinafter referred to by the variety name 'CIFZ0058'.

'CIFZ0058' is a product of a planned breeding program. The new cultivar has medium (1.75 inch) sized purple decorative flowers, a compact sized plant with round mound habit and a natural season response in early September.

'CIFZ0058' originated from cross in November 2008 in Tenjo, Columbia. The female parent was the red colored variety 'Zanmufive', U.S. Pat. No. 19,791, commercially known as 'Five Alarm'.

Compared to the female parent, 'CIFZ0058' has:

1) Similar flower type that is smaller in size with purple flower color not red like 'Five Alarm'
2) Natural season response is a couple days faster and blackcloth response is similar to 'Five Alarm'
3) Similar plant height but less plant width and rounder plant habit than 'Five Alarm'

The male parent was the unpatented purple coloured selection from own breeding '04-M277'.

Compared to the male parent, 'CIFZ0058' has:

1) Similar flower size and flower color with less disc florets than the male parent
2) Similar natural season and blackcloth response as the male parent
3) Similar plant height and plant habit as the male parent
4) Longer lasting flowers than the male parent The resultant seed was sown in June 2013 in Gilroy, Calif.

The first act of asexual reproduction of 'CIFZ0058' was accomplished when stem tip vegetative cuttings were propagated from the initial selection, this initial selection took place in Oct. 2, 2013 in Monroeville, N.J.

BRIEF SUMMARY OF INVENTION

Horticultural examination of plants grown from cuttings of the plant initiated in January 2014 in Mebane, N.C. and continuing thereafter, has demonstrated that the combination of characteristics as herein disclosed for 'CIFZ0058' are firmly fixed and are retained through successive generations of asexual reproduction.

'CIFZ0058' has not been observed under all possible environmental conditions. The phenotype may vary significantly with variations in environment such as temperature, light intensity and day length.

'CIFZ0058' has not been made publicly available prior to the effective filing date of this application, notwithstanding any disclosure that may have been made less than one year prior to the effective filing date of this application by the inventor or another who obtained 'CIFZ0058' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0058' with colors being as true as possible with an illustration of this type. The photographic drawing shows in FIG. 1 a close view of flower of the new variety and in FIG. 2 a flowering plant from an indoor trial.

Figure 2:
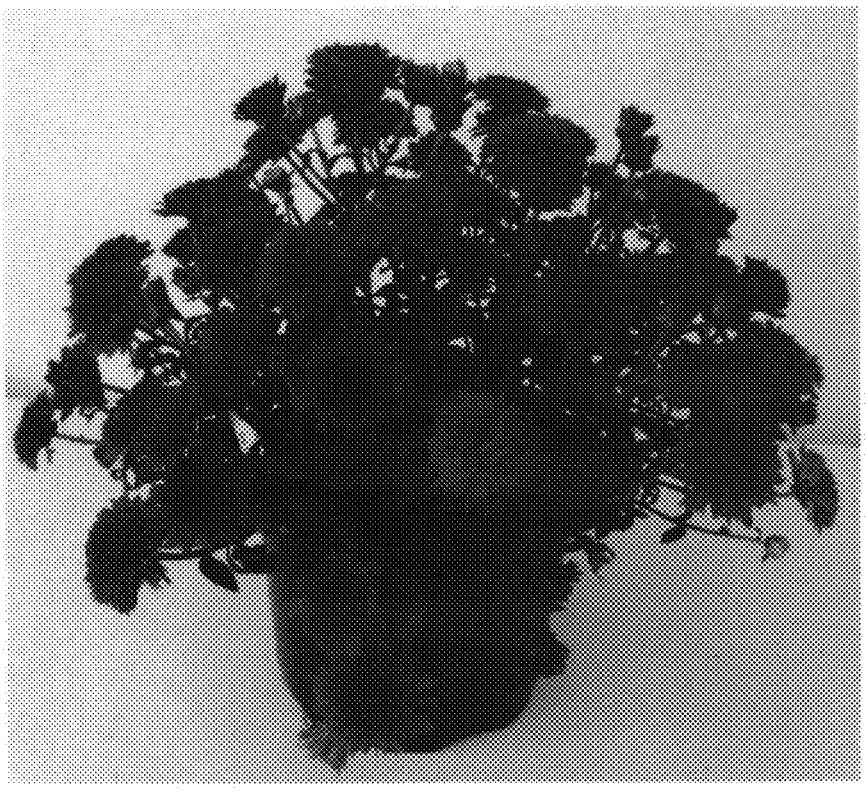

The aforementioned photographs: FIG. 1, as well as FIG. 2, were taken in August 2016 both showing a plant from the same blackcloth indoor trial in Gilroy, Calif.

These plants were about 9 weeks of age. One rooted cutting per pot had been planted in a 6 inch pot in week 24, not pinched. Shortday blackcloth treatment was applied from week 25 on. Plants started flowering in August.

DETAILED BOTANICAL DESCRIPTION

The measurements were taken in Gilroy, Calif. in August 2016 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0058' AND 'Empire Symphony'

| | 'CIFZ0058' | 'Empire Symphony', U.S. Plant Pat. No. 8,782 |
|---|---|---|
| Flowering response (natural): | Same, except in south U.S. (there it is one week faster) | Same, except in south U.S. (there it is one week slower) |
| Flowering response (blackcloth): | 1 week faster | 1 week slower |
| Uniformity of flowering: | Very uniform | Not very uniform |
| Flower color: | Darker color | Lighter color |
| Flower shape: | Similar | Similar |
| Flower size: | Smaller | Larger |

TABLE 2

DIFFERENCES BETWEEN THE NEW VARIETY 'CIFZ0058' AND 'Brilliance Pink'

| | 'CIFZ0058' | 'Brilliance Pink', No. U.S. Plant Pat. No |
|---|---|---|
| Flowering response (blackcloth): | Same | Same |
| Flowering response (natural): | 1 week faster | 1 week slower |
| Flower longevity: | Longer | Shorter |
| Flower color: | Darker color | Lighter color |
| Flower shape: | Similar | Similar |
| Flower size: | Bit smaller | Bit bigger |
| Plant habit or size: | Similar | Similar |

Plant:

*Form, growth and habit.*—Herbaceous garden-type, stems upright and outwardly spreading, freely branching, strong and moderately vigorous growth habit.

*Plant height (above soil).*—9-12 cm.

*Plant height (inflorescence included).*—13-17 cm.

*Plant width.*—29-31 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS 138A.

*Mature leaf, color lower surface.*—RHS 147B.

*Length.*—3.2-3.9 cm.

*Width.*—2.6-2.9 cm.

*Shape.*—Ovate.

*Base shape.*—Attenuate.

*Apex shape.*—Acute.

*Margin.*—3 main lobes, irregularly serrated.

*Texture, upper surface.*—Bifid hairs.

*Texture, lower surface.*—Bifid hairs.

*Color of veins, upper surface.*—RHS 141B.

*Color of veins, lower surface.*—RHS 138B.

*Pattern of veining.*—Palmate.

*Petiole color.*—RHS 137B.

*Petiole length.*—1.5-1.8 cm.

*Diameter.*—0.5-0.2 cm.

*Texture.*—Covered with bifid hairs.

Stem:

*Quantity of main branches per plant.*—7-10.

*Color of stem.*—RHS 138B.

*Length of stem.*—2-4 cm.

*Diameter.*—0.3-0.5 cm.

*Length of internodes.*—0.25-0.5 cm.

*Texture.*—Bifid hairs.

*Color of peduncle.*—RHS 138B.

*Length of peduncle.*—5.5-6.5 cm.

*Peduncle diameter.*—0.15 cm.

*Texture.*—Bifid hairs.

Inflorescence:

*Type.*—Compositae, solitary, decorative-type inflorescences borne terminally above foliage, ray florets arranged on a capitulum.

*Quantity of short days to flowering (response time).*—Approximately 5 weeks.

*Natural season flowering.*—Early September.

*Quantity of inflorescences per plant.*—70-90, with many small buds developing.

*Lastingness of individual blooms on the plant.*—About seven weeks from first color.

*Fragrance.*—Slightly spicy.

Bud (when showing color):

*Color.*—RHS 71A.

*Length.*—1.1-1.4 cm.

*Width.*—1.0-1.3 cm.

*Shape.*—Oblate.

Immature inflorescence:

*Diameter.*—2.2-3.0 cm.

*Color of ray florets, upper surface.*—RHS 61A.

*Color of ray florets, lower surface.*—RHS 61A, overlain with RHS 155A.

Mature inflorescence:

*Diameter.*—3.4-3.7 cm.

*Depth.*—1.5-2.0 cm.

*Total diameter of disc.*—0.5 cm.

*Receptacle color.*—RHS 145B.

*Receptacle height.*—0.3 cm.

*Receptacle diameter.*—0.15 cm.

Ray florets:

*Average quantity of florets.*—Between 150 and 180 in many whorls.

*Color of florets, upper surface.*—Between RHS 64A and RHS 64B.

*Color inner surface.*—RHS 64A overlain with RHS 155A.

*Length.*—1.2-1.7 cm.

*Width/diameter.*—0.4-0.6 cm.

*Shape.*—Oblong to elliptical.

*Apex shape.*—Emarginate.

*Base shape*.—Attenuate.
*Margin*.—Entire.
*Texture, upper surface*.—Smooth.
*Lower surface*.—Smooth.

Disc florets:
*Average quantities of florets*.—15-20.
*Colour of florets*.—RHS 1B, or slightly more greenish.
*Length*.—0.2-0.35 cm.
*Width*.—0.1 cm.
*Shape*.—Tubular, elongated.
*Apex shape*.—Acute, 5 pointed.

Phyllaries:
*Quantity*.—Approximately 20.
*Color, upper surface*.—RHS 137B.
*Color, lower surface*.—RHS 137C.
*Length*.—0.5-0.7 cm.
*Width*.—0.15-2.0.
*Shape*.—Lanceolate.
*Apex shape*.—Acute.
*Base*.—Fused.
*Margins*.—Entire, some with papery edges.
*Texture, upper surface*.—Glabrous.
*Texture, lower surface*.—Bifid hairs.

Reproductive organs:
*Pistil*.—One, found on both types of florets.
*Length*.—0.5 cm.
*Style color*.—RHS 1C.
*Style length*.—0.35 cm.
*Stigma color*.—RHS 7D.
*Stigma shape*.—Bi-parted.
*Ovary color*.—RHS 145C.
*Ovary length*.—0.15 cm.
*Ovary width*.—0.1 cm.

Androecium:
*Stamens*.—4, found on only the disk florets.
*Color of filaments*.—RHS 155C.
*Length filaments*.—0.2 cm.
*Anther color*.—RHS 9A.
*Anther length*.—0.1 cm.
*Anther shape*.—Oblong.
*Color of pollen*.—RHS 9A.
*Pollen amount*.—Sparse.
*Fertility/seed set*.—Has not been determined to date.
*Disease/pest resistance*.—Has not been determined to date.

What is claimed is:

1. A new and distinct variety of *Chrysanthemum* plant named 'CIFZ0058' substantially as illustrated and described herein.

* * * * *